(12) United States Patent
Kockan

(10) Patent No.: US 9,241,620 B1
(45) Date of Patent: Jan. 26, 2016

(54) USER AWARE DIGITAL VISION CORRECTION

(71) Applicant: DELL PRODUCTS, L.P., Round Rock, TX (US)

(72) Inventor: Sinem Kockan, Austin, TX (US)

(73) Assignee: DELL PRODUCTS, L.P., Round Rock, TX (US)

( * ) Notice: Subject to any disclaimer, the term of this patent is extended or adjusted under 35 U.S.C. 154(b) by 0 days.

(21) Appl. No.: 14/446,408

(22) Filed: Jul. 30, 2014

(51) Int. Cl.
| | |
|---|---|
| *A61B 3/02* | (2006.01) |
| *A61B 3/00* | (2006.01) |
| *A61B 3/032* | (2006.01) |
| *G06K 9/00* | (2006.01) |
| *G06F 3/0484* | (2013.01) |
| *G06F 3/0482* | (2013.01) |
| *G06F 17/30* | (2006.01) |

(52) U.S. Cl.
CPC .............. *A61B 3/0033* (2013.01); *A61B 3/0025* (2013.01); *A61B 3/032* (2013.01); *G06F 3/0482* (2013.01); *G06F 3/04842* (2013.01); *G06F 17/30876* (2013.01); *G06K 9/00255* (2013.01); *G06K 9/00288* (2013.01)

(58) Field of Classification Search
CPC ...... A61B 5/6898; A61B 5/7475; A61B 1/05; A61B 3/113; A61B 5/68
USPC .................. 351/239, 246, 240, 241, 242, 223
See application file for complete search history.

(56) References Cited

U.S. PATENT DOCUMENTS

| | | | | |
|---|---|---|---|---|
| 2008/0309879 | A1* | 12/2008 | Hirji ...................... | A61B 3/032 351/223 |
| 2013/0128229 | A1* | 5/2013 | Huang ..................... | G06K 9/46 351/239 |

* cited by examiner

*Primary Examiner* — Hung Dang
(74) *Attorney, Agent, or Firm* — Isidore PLLC

(57) ABSTRACT

A method, a system, and an information handling system dynamically provide individualized dynamic digital display correction for users of an electronic device. An information handling system detects a login of a first user profile that is associated with a first user. The information handling system then determines whether the first user profile has an associated first vision profile. In response to the first user profile having an associated first vision profile, a vision correction value associated with the first user is identified and a first change in image characteristics which may be applied to a graphical user interface (GUI) in order to achieve the vision correction value is calculated. A size of the display of the information handling system is detected and the first change in image characteristics is further adjusted based on this size before the adjusted image characteristic in image characteristics is applied.

20 Claims, 12 Drawing Sheets

USER AWARE DIGITAL VISION CORRECTION

BACKGROUND

1. Technical Field

The present disclosure generally relates to information handling systems and in particular to an improved method for providing a modified graphical user interface on an information handling system that compensates for a vision impairment of a user.

2. Description of the Related Art

As the value and use of information continue to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Among the people who utilize information handling systems are a large subset of people who have vision problems, such as presbyopia or hyperopia conditions of the eye. Persons with vision problems frequently require vision correction devices such as eyeglasses (or glasses for short) or contact lenses (or contacts for short) to correctly view text and images on displays of the information handling systems they utilize, e.g., with tablet computers, electronic reading devices, smartphones, and laptop computers. Displays of these types of information handling systems are catered to only users with ideal vision and the displays do not provide adjustments to displayed text and images to enable users with vision problems to view content without their vision correction devices.

BRIEF SUMMARY

Disclosed are a method, a system, and an information handling system for dynamically providing individualized digital display correction of displayed content for users having one or more vision problems. The method is implemented in an information handling system having a processor. The method comprises the information handling system detecting a login of a first user profile (of one or more user profiles) that is associated with a first user. In response to detecting the login of the first user profile, the method includes determining whether the first user profile has an associated first vision profile. In response to the first user profile having an associated first vision profile, a vision correction value associated with the first user is identified from the first vision profile and a first change in image characteristics to achieve the vision correction value on a graphical user interface (GUI) is calculated. Additionally, a size of the display of the information handling system is detected and the first change in image characteristics is further adjusted based on the size of the display. The method then includes applying the first change in image characteristics (or the adjusted image characteristics) to one or more contents of a GUI that is being displayed on a display of the information handling system.

In another embodiment, a distance between the first user and the data processing device is dynamically measured, via the user-facing camera. The first change in image characteristics applied to the GUI is dynamically adjusted (in real time) based on the distance between the first user and the data processing device.

In another embodiment, in response to determining the first user profile does not have an associated vision profile, an associated vision profile for the first user profile is established. The vision profile is established by setting a font size of the GUI to a largest size and initiating a vision test for each of the left eye and the right eye, which test includes: displaying a next character string of one or more of letters, numbers, and punctuation on the display, requesting the first user reenter the displayed character string, and receiving a user entry of the displayed character string. In response to receiving the user entry, the method includes determining whether the user entry is a match to the displayed character string. In response to determining the user entry is a match to the displayed character string, the font size of the GUI is adjusted to a next smaller size and the vision test is reinitialized at the next smaller size. In response to determining the user entry of the character string is not a match to the displayed character string: the vision profile of the first user profile is created and a plurality of vision characteristics based on a result of the vision test and a smallest size of the font size that was correctly identified by the first user is recorded within the vision profile.

In one embodiment, the method includes using at least one user-facing camera of the information handling apparatus to dynamically detect a presence of a current user of the information handling system and to perform a facial recognition of the current user of the information handling system. The method further includes comparing identifying characteristics from the facial recognition of the current user with facial recognitions profiles known to the information handling system in order to determine whether any of the facial recognition profiles include identifying characteristics that match characteristics from the facial recognition of the current user. In response to finding a match of identifying characteristics from a facial recognition profile of the current user from among the facial recognition profiles, the current user is identified and the first user profile is logged into one or more software or application running on the information handling system that generates the GUI.

In another embodiment, the method further includes detecting whether the first user is wearing corrective lenses. In response to detecting that the first user is wearing corrective lenses, application of the first change in image characteristics to the GUI is removed until detecting that the first user is no longer wearing the corrective lenses. In response to detecting that the first user is wearing corrective lenses before initializing the vision test, a request is issued to the first user to remove the corrective lenses before the vision test may proceed. Initialization of the vision test may be prevented until the information handling system detects that the first user is no longer wearing the corrective lenses. According to one aspect, users of contact lenses can be permitted to create a default baseline profile (with or without the vision test) while wearing their contact lenses. Separate corrective profiles can be created for the user without the contact lenses such that when use of contact lenses is detected, the baseline profile is loaded and when the user is not wearing the contact lenses, the corrective profile is loaded.

In another embodiment, the user entry of the character string can be a verbal recitation of the character string that is recorded via a microphone of the information handling system. A vocal analysis of the recorded verbal recitation may then be performed to determine a spoken content of the recorded verbal recitation, which is identified as the user entry of the character string.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description. The above as well as additional objectives, features, and advantages of the present disclosure will become apparent in the following detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
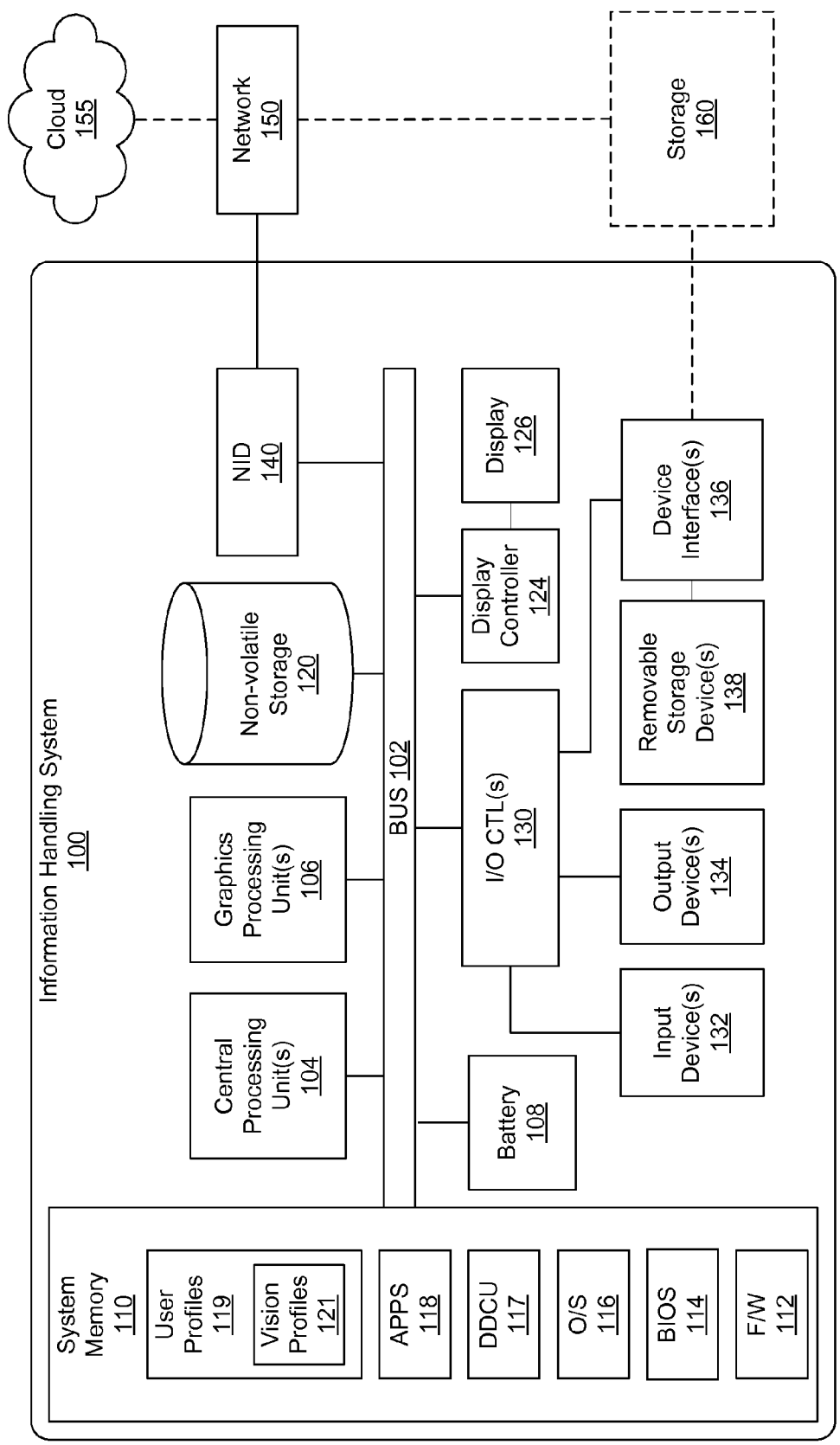
FIG. 1 provides a block diagram representation of an example information handling system within which certain aspects of the disclosure can be practiced, in accordance with one or more embodiments.

The illustrative embodiments provide a method, a system, and an information handling system for dynamically providing individualized dynamic digital vision correction for users of an electronic device. The method is implemented in an information handling system having a processor. The method includes the information handling system detecting a login of a first user profile, of one or more user profiles, that is associated with a first user. In response to detecting the login of the first user profile, the method further includes determining whether the first user profile has an associated first vision profile. In response to the first user profile having an associated first vision profile, a vision correction value associated with the first user is identified from the first vision profile and a first change in image characteristics to achieve the vision correction value on a graphical user interface (GUI) is calculated. Additionally, a size of the display of the information handling system is detected and the first change in image characteristics is further adjusted based on the size of the display. The adjusted image characteristics are applied to one or more contents of a Graphical User Interface (GUI) that is being displayed on a display of the information handling system.

As utilized herein, change in image characteristics and adjusted image characteristics refers to changes made in one or more of font (for text), size (e.g., for text and images) and blur effect. The term blur or blur effect can refer to graphic rescaling in a general sense or specifically to the blurring of images to accommodate a vision correction.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

Those of ordinary skill in the art will appreciate that the hardware components and basic configuration depicted in the following figures may vary. For example, the illustrative components within information handling system 100 are not intended to be exhaustive, but rather are representative to highlight essential components that are utilized to implement the present disclosure. For example, other devices/components may be used in addition to or in place of the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

Various aspects of the disclosure are described from the perspective of an information handling system and a display device of or for use with an information handling system. For purposes of this disclosure, an information handling system, such as information handling system 100, may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a handheld device, personal computer, a server, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, and a video display. The information handling system may also include one or more buses operable to transmit communications between the various hardware components.

With reference now to the figures, and beginning with FIG. 1, there is depicted a block diagram representation of an example information handling system (IHS) 100, within which one or more of the described features of the various embodiments of the disclosure can be implemented. Information handling system 100 includes at least one central processing unit (CPU) or processor 104 coupled to graphical processing unit(s) (GPU) 106 and system memory 110 via system interconnect bus 102. While provided in FIG. 1 as discrete units, in another embodiment GPU(s) 106 may be integrated devices within CPU(s) 104. System interconnect bus 102 can be interchangeably referred to as a system bus, in one or more embodiments. Also coupled to system interconnect bus 102 is nonvolatile storage 120, within which can be stored one or more software and/or firmware modules and one or more sets of data that can be utilized during operations of information handling system 100. These one or more software and/or firmware modules can be loaded into system memory 110 during operation of information handling system 100. Specifically, in one embodiment, system memory 110 can include therein a plurality of such modules, including one or more of firmware (F/W) 112, basic input/output system (BIOS) 114, operating system (OS) 116, digital display correction utility (DDCU) 117, application(s) 118, and user profiles 119. These software and/or firmware modules have varying functionality when their corresponding program code is executed by CPU 104 or secondary processing devices within information handling system 100. While user profiles 119 are illustrated within system memory 110, user profiles 119 may also be stored in external storage 160 and/or cloud network 155 and may be further accessible by IHS 100 and any other devices (not pictured) connected thereto.

DDCU 117 is a utility which executes within IHS 100 to provide logic that performs the various method and functions described herein. For simplicity, DDCU 117 is illustrated and described as a stand-alone or separate software/firmware/logic component, which provides the specific functions and methods described below. However, in at least one embodiment, DDCU 117 may be a component of or may be combined with or incorporated within OS 116 and/or one or more of applications 118.

In one embodiment IHS 100 further includes a battery 108 for powering IHS 100. IHS 100 may also include an interface (not pictured) for connecting to an alternating current (AC) or direct current power source for powering IHS 100 and/or charging battery 108.

IHS 100 further includes a display controller 124 for outputting display data to one or more display(s) 126. Display(s) 126 may further include any of touch monitors, televisions, and/or touch screens or displays with a digitizer component for receiving user touch and/or pen input. Additionally, display controller 124 may also receive input data, such as touch input and/or digitizer input, from display(s) 126. While display controller 124 is illustrated in FIG. 1 as a discrete component, in one embodiment display controller 124 may be incorporated within GPU(s) 106. Furthermore, while display 126 is illustrated in FIG. 1 as a discrete component within IHS 100, in one embodiment display controller 124 may be an externally and/or remotely connected display.

IHS 100 further includes one or more input/output (I/O) controllers 130 which support connection by and processing of signals from one or more connected input device(s) 132, such as a keyboard, mouse, hardware button(s), touch screen, infrared (IR) sensor, fingerprint scanner, or microphone. I/O controllers 130 also support connection to and forwarding of output signals to one or more connected output devices 134, such as audio speaker(s). Additionally, in one or more embodiments, one or more device interfaces 136, such as an optical reader, a universal serial bus (USB), a card reader, Personal Computer Memory Card International Association (PCMIA) slot, and/or a high-definition multimedia interface (HDMI), can be associated with IHS 100. Device interface(s) 136 can be utilized to enable data to be read from or stored to corresponding removable storage device(s) 138, such as a compact disk (CD), digital video disk (DVD), flash drive, or flash memory card. In one or more embodiments, device interfaces 136 can further include General Purpose I/O interfaces such as I²C, SMBus, and peripheral component interconnect (PCI) buses. Device interface(s) 136 can also be utilized to enable data to be read from or stored to external storage 160

Information handling system 100 comprises a network interface device (NID) 140. NID 140 enables IHS 100 and/or components within IHS 100 to communicate and/or interface with other devices, services, and components that are located external to information handling system 100. These devices, services, and components can interface with IHS 100 via an external network, such as example network 150, using one or more communication protocols. Network 150 can be a local area network, wide area network, personal area network, and the like, and the connection to and/or between network and IHS 100 can be wired or wireless or a combination thereof. Additionally, network 150 may also be further connected to other networks such as a cloud network 155. Alternatively IHS 100 may also directly connect to cloud network 155 via NID 140.

For purposes of discussion, network 150 is indicated as a single collective component for simplicity. However, it is appreciated that network 150 can comprise one or more direct connections to other devices as well as a more complex set of interconnections as can exist within a wide area network, such as the Internet.

Operating System 116 and/or one or more applications 118 running on IHS 100 enable IHS 100 to recognize a user and automatically adjusts image characteristics of a display and/or Graphical User Interface (GUI) of IHS 100 based on the user's vision characteristics so that the user may use IHS 100 optimally, regardless of undesirable vision characteristics of the user such as presbyopia or hyperopia. In response to IHS 100 dynamically detecting a specific user, IHS 100 automatically applies changes in image characteristics (i.e., sets a font size of the GUI and/or adjusts a level of blur effect and/or activates filtering algorithms) that are applied to a display 126 of IHS 100 in order to achieve a level of vision correction identified by a vision profile associated with that user. Improving a person's perceived vision by way of vision correction devices is sometimes colloquially referred to as "correcting vision" and/or "vision correction". Thus, IHS 100 addresses those users who need to wear eyeglasses or contact lenses by individually compensating ("correcting") vision problems/impairments of the users so that those users may more easily view images and text on the display 126 of (or connected to) IHS 100 without using vision correction device(s) (such as contact lenses or eyeglasses).

For each new user, a user profile 119 and an associated vision profile 121 (which may or may not be contained within the user profile itself) is created. The vision profile 121 includes information about user's right eye and left eye vision characteristics and/or the user's vision correction methods (e.g., whether user is a contact lens wearer or not). The vision characteristics may include vision measurements of and/or prescription information for each eye individually. To learn the user's vision characteristics, a vision test can be performed at IHS 100 or the profile can be created at and imported from another location, in one alternate embodiment. During the vision test, the user is asked to repeat back a character string comprising any combination of letters, numbers, symbols, and punctuation that is shown on the screen. In one embodiment, the vision test may be applied to both right eye and left eye separately. In another embodiment, the vision test may be terminated in response to determining the right eye and left eye do not provide the same vision characteristics and/or cannot be simultaneously corrected by IHS 100. The vision profile may also include eye correction prescription data and/or vision characteristics that are entered by the user or a health care professional such as an optometrist or ophthalmologist.

For each vision test performed, IHS 100 stores the conditions of the vision test (e.g., the display size and user's proximity to the display) to the user's profile with the user's vision characteristics. User profiles and vision profiles can be shared between multiple devices associated with and/or operated by a user, such that the user is able to use IHS 100 or any other electronic device and receive the same autonomous digital display correction. Once a user's vision characteristics are stored, the user may be recognized by IHS 100 during each use. IHS 100 automatically adjusts the image characteristics based on the contents of a user's vision profile, the device's display size, and/or the user's proximity to the display. In one embodiment, the vision profile may further use a smallest size of the font size that was correctly identified by the user during the vision test to calculate a change in image characteristics and or level of filtering applied to the GUI or display of IHS 100.

In one embodiment, the image characteristics of IHS 100 may not be adjusted while the user is wearing a vision correction device(s) (such as contact lenses or eyeglasses) unless the user agrees to start the digital display correction and/or removes the vision correction device(s). IHS 100 may also periodically or continually check for the user's continued usage/existence, and IHS 100 stops or adjusts the digital display correction if the user is not using IHS 100 or in response to another user operating IHS 100. IHS 100 also allows users to start or stop the digital display correction manually via voice commands or toggle of an option on a displayed GUI (such as a soft button) or actuation of a hardware button and/or input sensor.

In one embodiment, vision profiles 121 (or any individual component thereof) may be stored and/or updated locally and/or externally (such as within cloud 155). In addition to user profiles 119, vision profiles 121 may also be created, maintained, and/or updated by the user and/or any other authorized entities or health care professionals. Additionally, user profiles 119 and vision profiles 121 may be retrieved at, or transmitted to, any other electronic devices (which are also information handling systems) that are associated with, being used by, and/or accessible to the user and/or that are connected to one or more of IHS 100, network 150, storage 160, and/or cloud 155.

According to one aspect, users of contact lenses are permitted to complete the vision test while wearing their contact lenses. Separate profiles can be created for the user with the contact lenses on (a baseline profile) and without the contact lenses (a corrective profile) such that when use of contact lenses is detected by IHS 100, the baseline profile is loaded and when the user is not wearing the contact lenses, the corrective profile is loaded.

Figure 2:
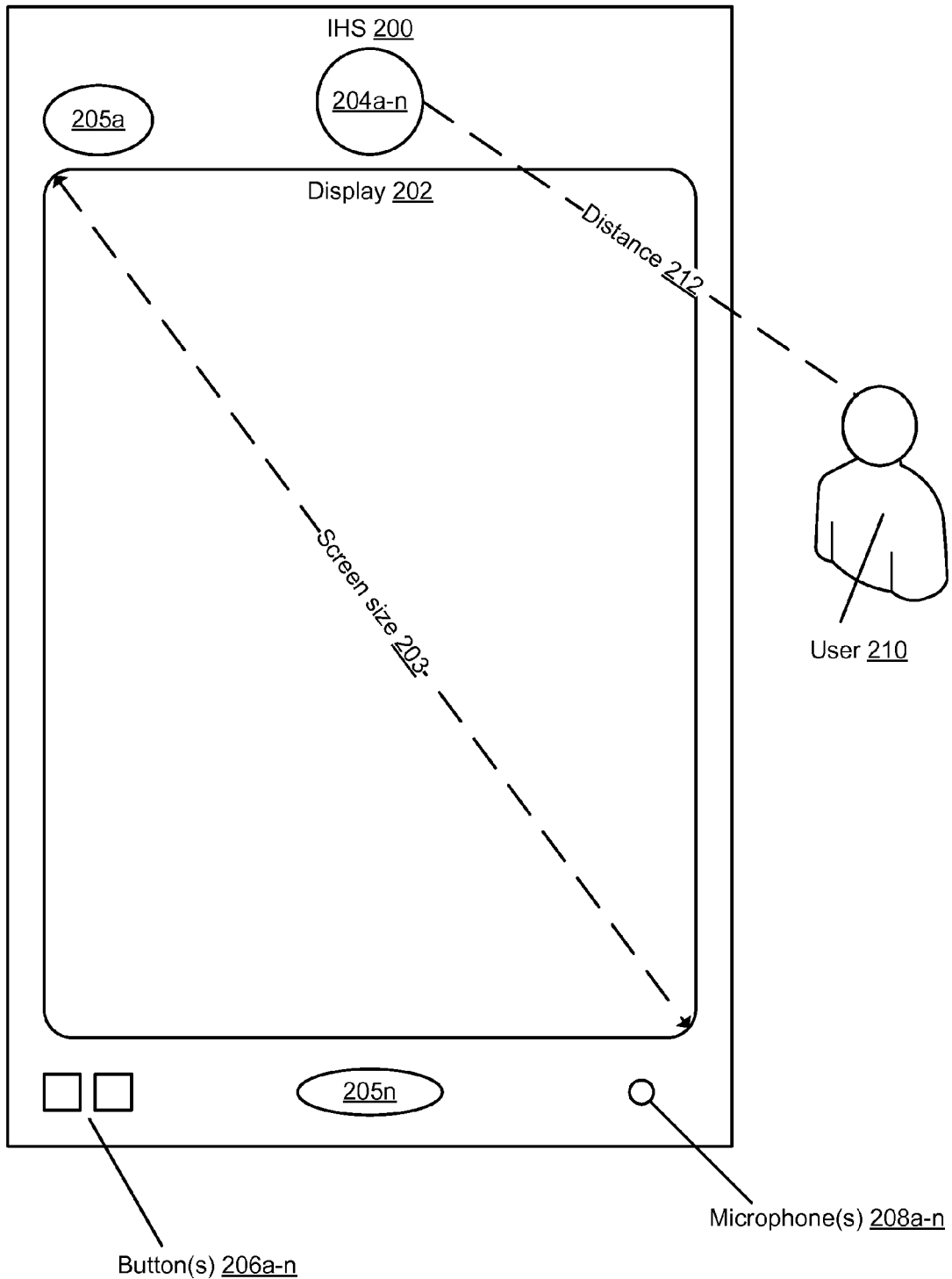
FIG. 2 illustrates an example information handling system for interfacing with at least one user, in accordance with one or more embodiments.

FIG. 2 illustrates an example information handling system 100 for interfacing with at least one user 210, in accordance with one or more embodiments. As shown, IHS 100 comprises several input devices and output devices for interacting with user 210. IHS 100 includes a display 202 that is capable of displaying a graphical user interface (GUI) output of IHS 100. In one embodiment a screen size 203 of display 202 may already be known to IHS 100 and/or may be retrieved from one or more internal or external storage of IHS 100 (e.g., non-volatile storage 120, removable storage device(s) 138, cloud 155, or storage 160). In another embodiment, screen size 203 may be determined by IHS 100 by reading Extended Display Identification Data (EDID) of display 202. Screen size 203 may be represented as a physical diagonal measurement of display 202, such as a measurement in inches or centimeters. In another embodiment, screen size or may be characterized as a total pixel count of the display 202 or a count of pixels in one or more directions/dimensions of display 202

In one embodiment, display 202 is a touch screen that is also capable of receiving touch input from a user of IHS 100 for interacting with a displayed GUI. A GUI displayed by IHS 100 on display 202 may be rendered by CPU(s) 104, GPU(s) 106, or any combination thereof. Furthermore, CPU(s) 104 and GPU(s) 106 may also be used to apply one or more image filtering techniques and/or image processing algorithms (e.g., a Fast Fourier Transform (FFT)) to one or more specific contents within a displayed GUI or the entire GUI itself.

In one embodiment, IHS 100 may also include cameras 204*a-n*, input sensors 205*a-n*, hardware buttons 206*a-n*, and microphones 208*a-n*. Cameras 204*a-n* may be used to detect and/or locate one or more users 210 that are proximate to IHS 100. Additionally, in one embodiment where IHS 100 comprises multiple cameras 204*a-n*, two or more cameras may be used to provide a more accurate location of user 210 and/or determine a current orientation of IHS 100 relative to user 210. Further still, cameras 204*a-n* may be used to measure a distance 212 between user 210 and IHS 100. Input sensors 205*a-n* may include one or more sensors for detecting a user such as a flash, an infrared (IR) sensor, a retinal scanner/reader, a fingerprint scanner/reader, a low-light sensor, heart-rate sensor, or an ultrasound sensor. Input sensors 205*a-n* may be used to collect biometric data on user 210. Input sensors 205*a-n* may also be used to measure the distance 212 between user 210 and IHS 100. Microphones 208*a-n* may be used to receive spoken input/commands from user 210. In one embodiment, multiple microphones 208*a-n* may be used to perform noise reduction of environmental sounds near user 210 to enhance vocal input from user 210. Hardware buttons 206*a-n* are selectable buttons which may be used to receive input from a user. In one embodiment hardware buttons 206*a-n* may also be integrated with one or more input sensors 205*a-n* (e.g. a fingerprint scanner) and/or be pressure sensitive. Hardware buttons 206*a-n* may also be directly associated with one or more functions of the GUI and/or functions of an OS, application, or hardware of IHS 100. In one embodiment hardware buttons 206*a-n* may include a keyboard.

Referring now to FIGS. 3-5, 7-8, and 10-12, there are illustrated flow charts of the methods for providing individualized dynamic digital display correction for users of an information handling system, according to one or more embodiments. Aspects of the methods are described with reference to the components of FIGS. 1-2. Several of the processes of the methods provided in FIGS. 3-5, 7-8, and 10-12 can be implemented by the CPU 104 executing software code of DDCU 117 within an information handling system. For simplicity in describing the methods below, the processes are generally described as being performed by the information handling system.

Figure 3:
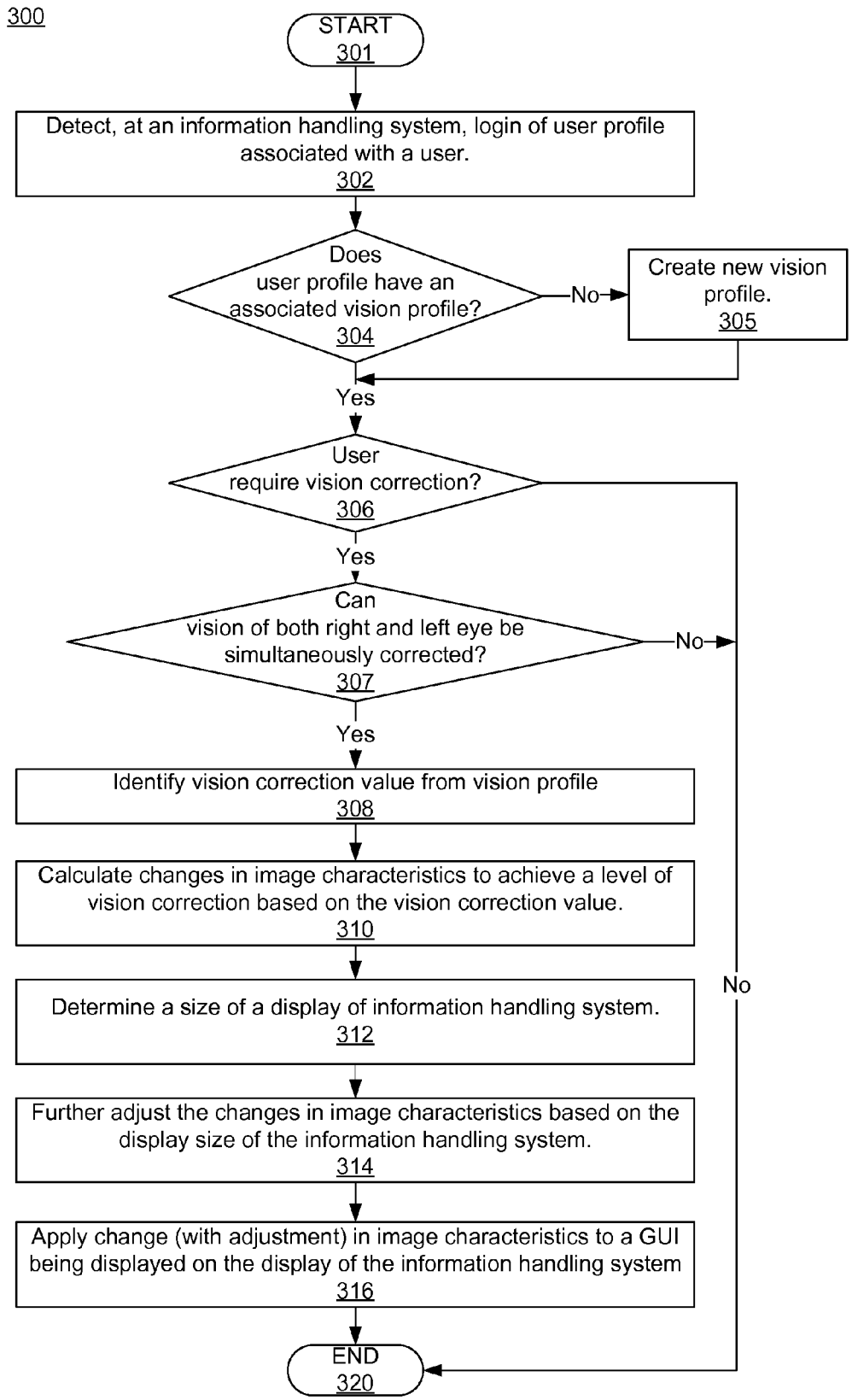
FIG. 3 is a flow chart illustrating a method for applying a change in image characteristics to a GUI being displayed on a display of an information handling system to compensate for a vision impairment of a user, in accordance with one or more embodiments.

Referring now to FIG. 3, there is depicted a high-level flow-chart illustrating a method 300 for applying a change in image characteristics to a GUI being displayed on a display of an information handling system to compensate for a vision impairment of a user, in accordance with one or more embodiments of the present disclosure. Method 300 commences at initiator block 301, which proceeds to block 302 at which point the information handling system detects the login of a user profile associated with a user. A user profile may be logged into IHS 100 by any of the methods described herein (e.g., username/password login, pin login, gesture login, facial recognition login, biometric data login) and/or any other methods known in the art. The method for logging in a user to the information handling system is described in greater detail below in method 400 of FIG. 4. At block 304 IHS 100 determines if the user profile that was logged in has a vision profile associated therewith. In response to determining that the user profile that was logged does have an associated vision profile, the method continues to block 306. In response to determining that the user profile that was logged does not have an associated vision profile, the method continues to block 305 where a new vision profile is created before the process continues to block 306. According to one embodiment, when the user is wearing contact lenses, no vision profile is created for that user, unless the user desires to create a corrective vision profile for use when not wearing his/her contact lenses. The user's vision profile is created when the user is not wearing contact lenses. In the implementation where the user is wearing the contact lenses, regardless of having a vision profile, the method ends once the user's login is detected, and no vision profile is loaded. The method for creating a vision profile for a user is described in greater detail below in method 500 of FIG. 5.

At block 306 a determination is made from the vision profile associated with the user profile whether the user requires vision correction to properly view the GUI of IHS 100. In response to determining, from the vision profile, that the user does not require vision correction to properly view the GUI of IHS 100, the method terminates at block 320. In response to determining from the vision profile that the user requires vision correction to properly view the GUI of IHS 100, the method proceeds to block 307. At block 307 a determination is made from the vision profile associated with the user whether the user's right and left vision characteristics can be simultaneously corrected. In response to determining, from the vision profile, that both sides of the user's vision characteristics cannot be corrected by vision correction to properly view the GUI of IHS 100, i.e. the user has different right and left eye vision characteristics, the method terminates at block 320. In response to determining from the vision profile that the user's right and left eye characteristics can be simultaneously corrected, the method proceeds to block 308 where the vision correction value is identified and acquired from the vision profile. At block 310, IHS 100 calculates a baseline change in image characteristics to be applied to contents within a displayed GUI of IHS 100 to achieve a level of vision correction specified by the vision correction value that compensates for vision problems/impairments of the user. The method then continues to block 312 where the display size of the display (e.g. display 203) of IHS 100 is determined. At block 314 the change in image characteristics to be applied to contents within the displayed GUI is further adjusted for more or less changes as is appropriate to achieve the level of vision correction specified by the vision correction value at the determined display size of the display of IHS 100. The change in image characteristics or the adjusted image characteristics (when adjustments are made) is then applied to the contents within the displayed GUI. The method then ends at block 320.

Figure 4:
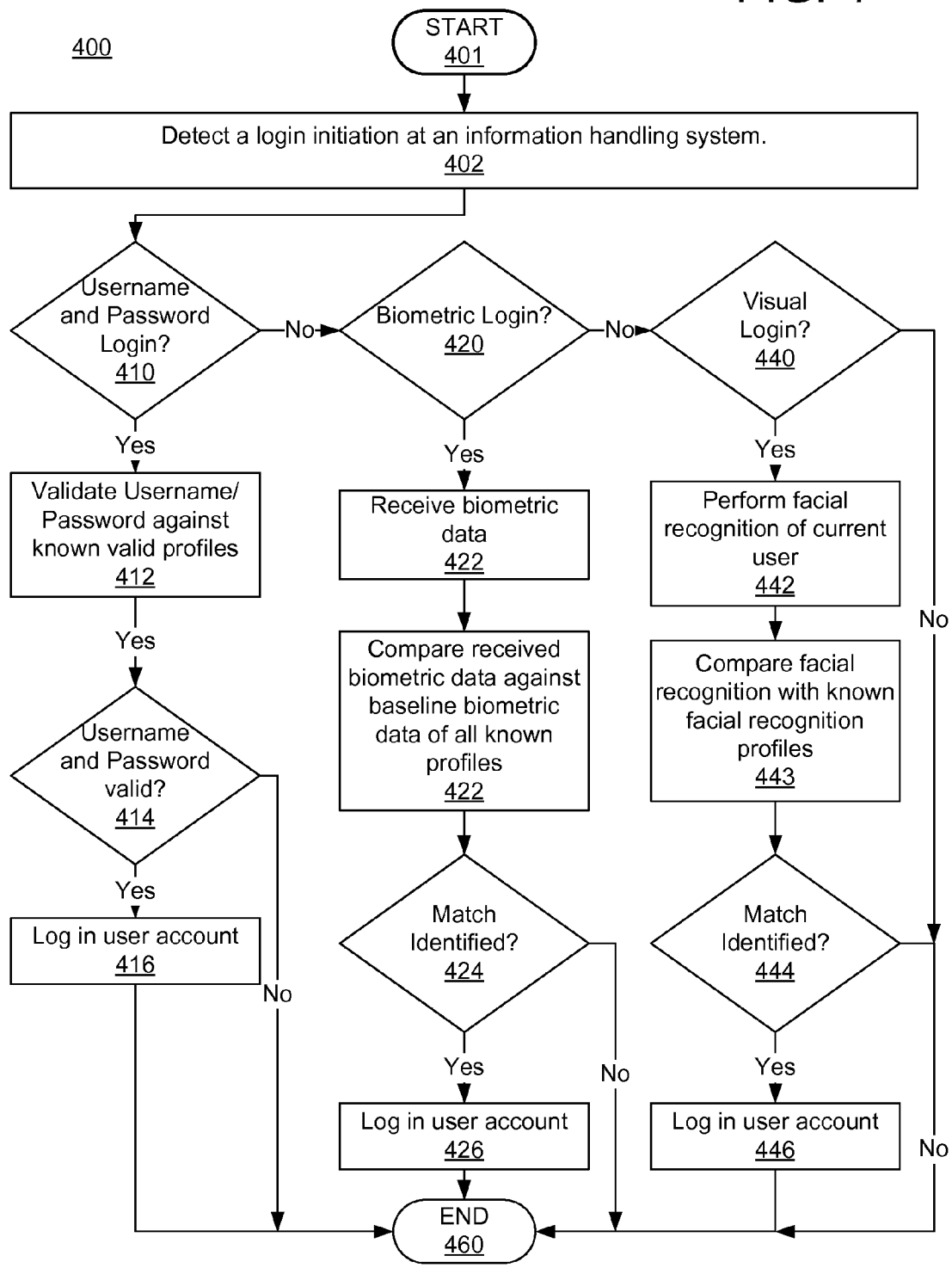
FIG. 4 is a flow chart illustrating a method for logging a user into an information handling system, in accordance with one or more embodiments.

Referring now to FIG. 4, there is depicted a high-level flow-chart illustrating a method 400 for logging a user into an information handling system, in accordance with one or more embodiments, in accordance with one or more embodiments of the present disclosure. Method 400 commences at initiator block 401, which proceeds to block 402 where a login initiation by a user is detected. In one embodiment the login initiation includes IHS 100 receiving a selection of one particular login method from a user of IHS 100 (e.g., receiving a request for a fingerprint login). In another embodiment the login initiation includes IHS 100 dynamically detecting the presence of a user, for example, by identifying a user using a camera (e.g. cameras 204a-n), which may be always-on or triggered by a user and/or routine of IHS 100. In still another embodiment the login initiation includes the actuation of a microphone (e.g., microphones 208a-n) or sensor (e.g., input sensors 205a-n) and/or receiving biometric data of a user from a microphone or sensor.

In response to detecting the login initiation, IHS 100 determines if the login initiation is a login to a user profile associated with the user (block 410). In response to determining the login initiation is for a username and password login to the user profile associated with the user, IHS 100 receives a username and password combination from a user and attempts validation of the received username and password credentials using known valid username and password credentials that are locally or remotely accessible by IHS 100 (block 412). At block 414 IHS 100 determines if the received username and password credentials are valid. In response to the received username and password credentials being valid, the user profile is logged in to IHS 100 (block 416) and the login method ends at block 460. In response to the received username and password credentials not being valid, the process terminates at block 460.

In response to determining the login initiation is not for a username and password login to the user profile associated with the user, a determination is made whether the login initiation is for a biometric login (block 420). In response to determining the login initiation is for a biometric login the biometric data is received (block 422). In another embodiment, receiving the biometric data can be part of the login initiation. At block 422 the received biometric data is compared against baseline biometric data within known user profiles that are locally or remotely accessible by IHS 100 to identify a match. In response to identifying a match (block 424), the user profile is logged in to IHS 100 (block 426) and the login method ends at block 460. In response to IHS 100 not being able to find a match for the received biometric data, the process terminates at block 460.

In response to determining the login initiation is not for a username and password login or a biometric login, a determination is made whether the login initiation is a visual login attempt via a camera(s) (e.g. cameras 204a-n) of IHS 100 (block 440). In response to determining the login initiation is for a visual login, a facial recognition analysis is performed of a nearby user using the camera(s) (block 442). In another embodiment, detecting a particular nearby user or the presence of any nearby person may be part of the login initiation. At block 443, data obtained during the facial recognition analysis is compared against facial recognition profiles stored within known user profiles that are locally or remotely accessible by IHS 100 to identify a match. In response to identifying a match (block 444), the user profile is logged in to IHS 100 (block 446) and the login method ends at block 460. In response to IHS 100 not being able to find a match to the data obtained during the facial recognition analysis, the process terminates at block 460. In the steps above, it should be noted that in one embodiment, in response to a failed login attempt, IHS 100 may also prompt a user to create a profile. In yet another embodiment, in response to a failed login attempt, the user may be prompted to retry the login attempt.

Figure 9:
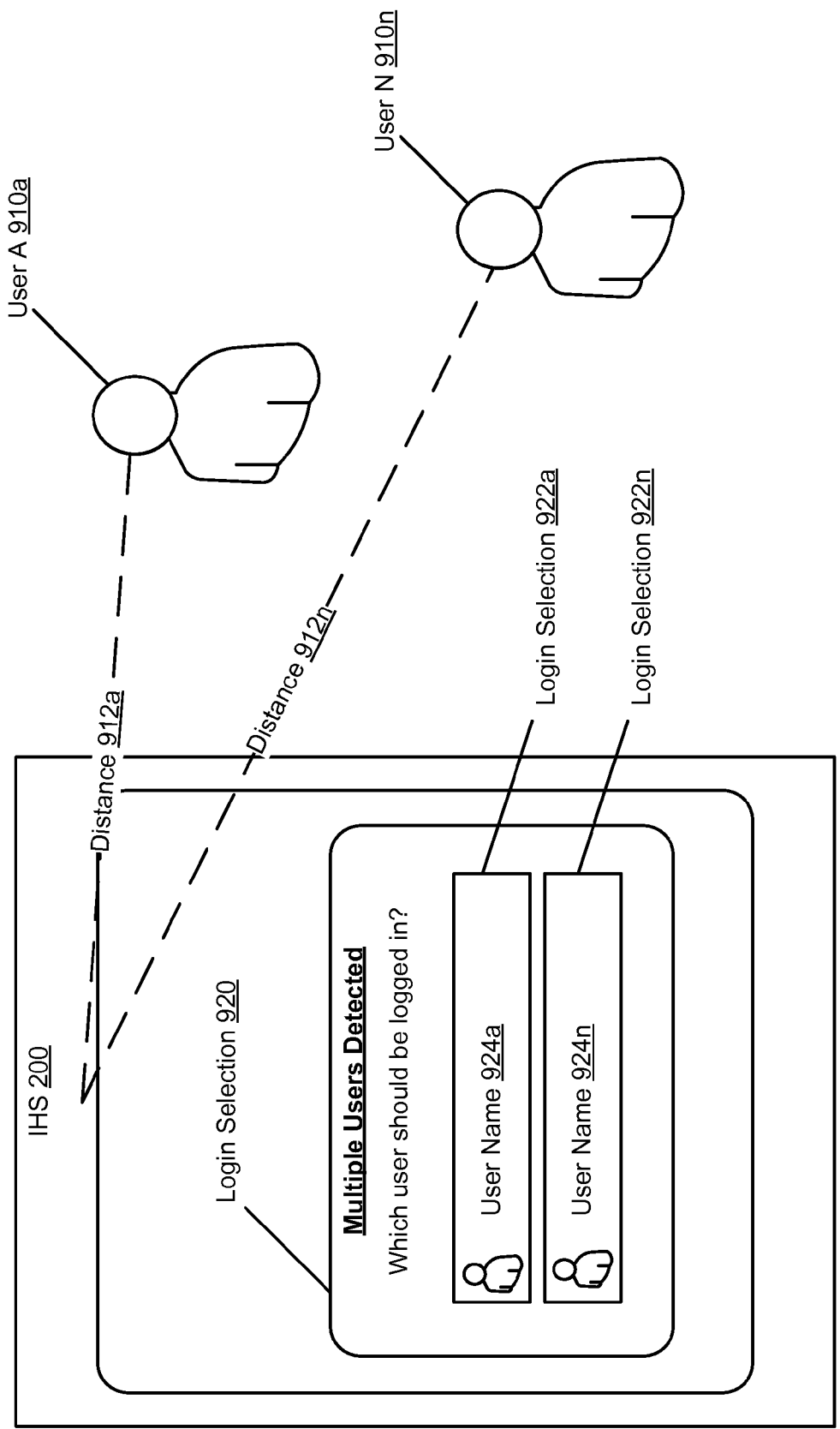
FIG. 9 illustrates an example graphical user interface for detecting and selecting a current user of multiple users of an information handling system, in accordance with one or more embodiments.

Referring now to FIG. 9, there is illustrated an example graphical user interface for detecting and selecting a current user from among multiple users of an information handling system, in accordance with one or more embodiments of the present disclosure. FIG. 9 provides a login selection 920 that may be dynamically displayed on a display of IHS 100 at any time when multiple users are present. In another embodiment, login selection 920 may only be displayed in response to receiving a request from one or more of users 910a-n. Login selection 920 provides, for each detected user, 910a-n, a login selection box 922a-n that identifies a user name of each user 910a-n which may be selected to establish an active user that is logged in to IHS 100. Login selection boxes 922a-n may be actuated by any of a voice selection, a touch on a touch screen of IHS 100, selection via a keyboard or mouse, etc. The user name of each user 910a-n may be any of a real name(s), an identifier, a handle, an electronic mail address, etc.

In another embodiment, in lieu or in addition to login selection 920, IHS 100 may also detect a current distance 912a-n between IHS 100 and each user 910a-n. IHS 100 may then autonomously login a closest user 910a-n. Furthermore, IHS 100 may maintain a user that is currently logged-in so long as that user is the closest user to IHS 100 and/or so long as that user is still detected by IHS 100.

Figure 5:
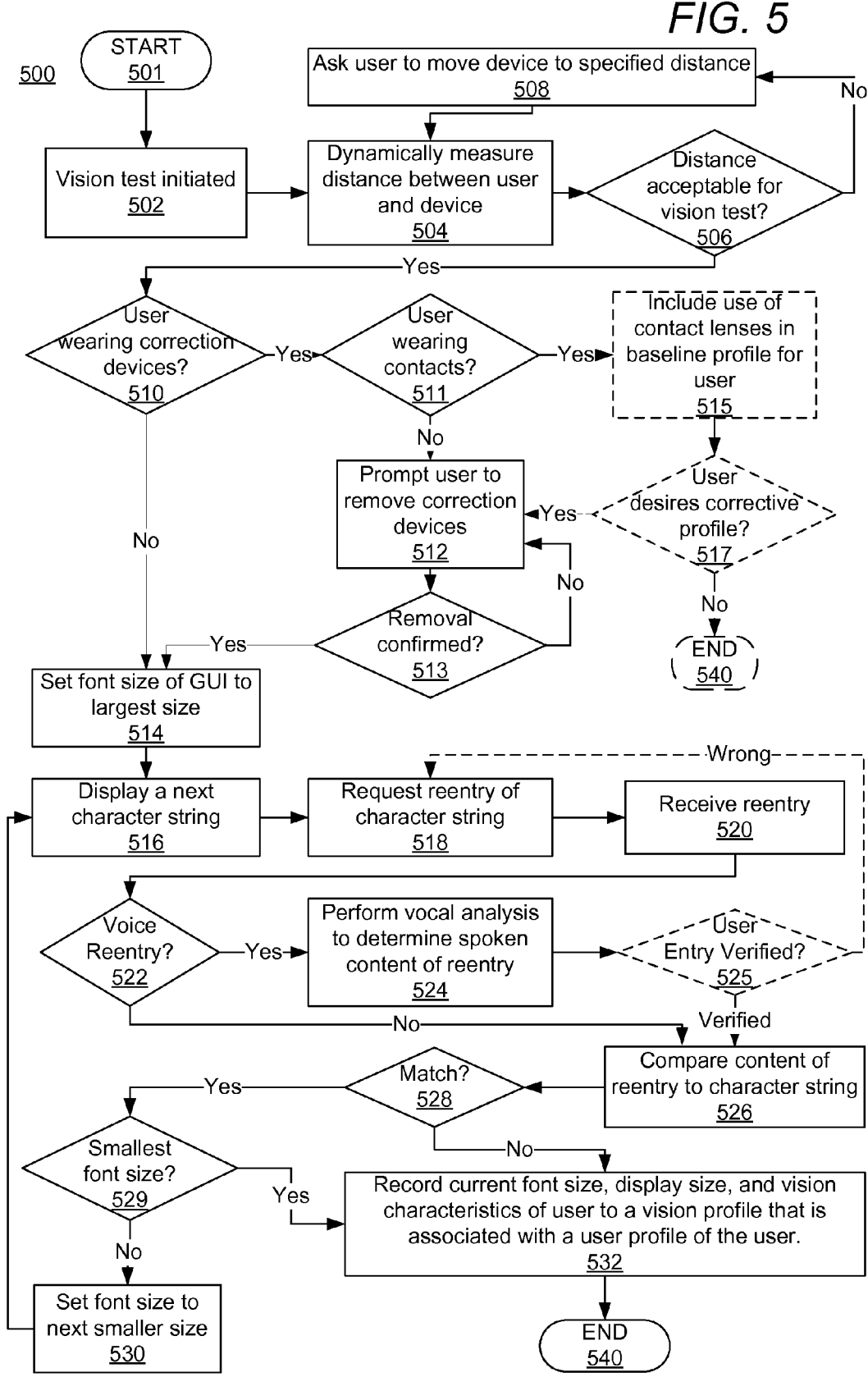
FIG. 5 is a flow chart illustrating a method for performing a vision test via an information handling system, in accordance with one or more embodiments.

Referring now to FIG. 5, there is depicted a high-level flow-chart illustrating a method 500 for performing a vision test via an information handling system, in accordance with one or more embodiments of the present disclosure. Method 500 commences at initiator block 501, which proceeds to block 502 where the vision test is initiated. The vision test may be automatically initiated by IHS 100 (e.g., in response to detection or a user and/or login of a user) or may be manually initiated (e.g. responsive to receiving a user request). In one embodiment the vision test must first be accepted by the user, including any terms or conditions of the vision test. After initiation of the vision test, a distance between the user and the device is dynamically measured (block 504). At block 506 IHS 100 determines whether the measured distance between the user and IHS 100 is acceptable for the vision test. In response to determining the measured distance is not acceptable for performing the vision test, IHS 100 issues an alert that requests the user move the device closer to the user or further from the user, as appropriate. The alert may include one or more of audio, visual, and/or vibration feedback. In one embodiment, this alert may also include an indication of an acceptable distance or range of distances for conducting the vision test and/or a real-time current distance between the user and IHS 100. The process then continues back to block 504.

In response to determining that the measured distance is acceptable for performing the vision test, the method continues to block 510 where a determination is made whether the user is wearing vision correction devices such as contacts or glasses. In one embodiment, this detection may be performed autonomously by scanning the face of the user using cameras and/or sensors of IHS 100 to ascertain whether the user is wearing vision correction devices. In another embodiment, a prompt may be issued, which requires the user tender a response of whether the user is wearing vision correction devices before the method may proceed. In response to determining that the user is wearing vision correction devices, a next determination is made at block 511 whether the user is wearing contact lenses. In response to determining that the user is wearing correction devices, which are not contact lenses (e.g., the user is wearing glasses), the user is prompted, using one or more of audio, visual, and/or vibration feedback, to remove the vision correction devices (block 512). The method then proceeds to block 513 where IHS 100 confirms whether the user removed the vision correction devices. In one embodiment, IHS 100 may automatically detect the removal of the vision correction devices. In another embodiment, IHS 100 may receive a confirmation from the user that the vision correction devices have been removed. In response to confirming the vision correction devices have not been removed, the method loops back to block 512. In response to confirming the removal of the vision correction devices, the method continues to block 514.

In one embodiment, users of contact lenses are permitted to complete the vision test with their contact lenses removed. Separate profiles can be created with the contact lenses and without the contact lenses such that when use of contact lenses is detected, the baseline profile is loaded and when that user is not wearing the contact lenses, the corrective profile is loaded. According to the illustrative embodiment, the method can include several optional blocks, indicated with dashed lines, that enable a profile establishment of a corrective user profile when the user is wearing contacts but desires to have a profile that allows for use of the HIS 100 while the user is not wearing his/her contacts. Thus, as shown, in response to determining at block 511 that the user is wearing correction devices, which are contact lenses, the current profile (assuming one exists) is tagged or updated to be a baseline profile (block 515) and a next determination can be made at block 517, whether the user desires to also create a corrective profile. The determination at block 517 can be based on a query or prompt to the user and response received from the user to that query or prompt for creation of a corrective profile. When the user desires to create a corrective profile, the method returns to block 512. However, when the user does not desire to create a corrective profile, the method terminates at block 540 without recording a vision profile for that user profile. In one implementation where the optional blocks are not provided, the method may terminate at block 540 in response to detecting that a user is wearing contacts. In another implementation where the optional blocks are not provided, in response to detecting that a user is wearing contacts, the usage of the contacts may be ignored and the method continues to block 512.

In response to determining that the user is not wearing vision correction devices, the current font size of a GUI being displayed on a display of IHS 100 is set to a largest size and a vision test is commenced (block 514). To complete the vision test, the following sequence of steps is repeated for both right and left eye separately. At block 516 a next character string is displayed on the GUI at the current font size. After displaying the character string, IHS 100 requests the user reenter the character string (block 518). A user entry of the character string is then received at IHS 100 from the user (block 520). The user entry of the character string may be typed into IHS 100 via a virtual or physical keyboard and/or may be received as a spoken voice recorded by one or more microphones of IHS 100. After receiving the user entry, IHS 100 then determines whether the user entry was a spoken voice recording by the user (block 522). In response to determining the user entry was not a spoken voice recording, the method continues to block 526. In response to determining the user entry was a spoken voice recording, the method continues to block 524 where IHS 100 performs an audio analysis of the spoken voice recording by the user to determine a content of the user entry. Once the audio analysis has been completed, method can optionally include repeating the user entry to the user to verify that the entry is what was intended by the user (optional block 525). When the entry is verified, the method proceeds to block 526. However, when the entry is not verified (i.e., a wrongly analyzed or entered entry), the method returns to block 518. This optional block enables correction of voice recognition or keystroke errors to not adversely affect the analysis of the user's vision correction profile. At block 526 the content of the user entry is compared to the content of the character string. At block 528 IHS 100 determines whether the content of the user entry matches the content of the character string. When the content of the user entry does not match the content of the character string, the process continues to block 532 where the current font size, the distance between the user that the vision test was performed at, the screen size of IHS 100, and one or more vision characteristics of the user based on the vision test are recorded to the vision profile that is associated with the user profile corresponding to the user. The process then terminates at block 540.

In response to determining that the content of the user entry matches the content of the character string, the method continues to block 530 where IHS 100 determines whether the current font size is the smallest font size (block 529). In response to determining the current font size is not the smallest font size, the current font size of the GUI is set to a next smaller size (block 530) and the method loops back to block 516 in an iterative fashion. In response to determining the current font size is the smallest font size, the method continues to block 532.

While the above method 500 describes recording a current size of the font of the GUI in response to reaching a smallest font size or a user entry by a user not matching a character string, it should be appreciated that in other embodiments the current font size that is recorded to the vision profile may be the largest font size if the user never entered a correct user entry or a smallest size font that the user correctly entered in a user entry. In one embodiment, the user may be asked to confirm a user entry prior to IHS 100 comparing the content of the user entry with the content of the character string.

Figure 6:
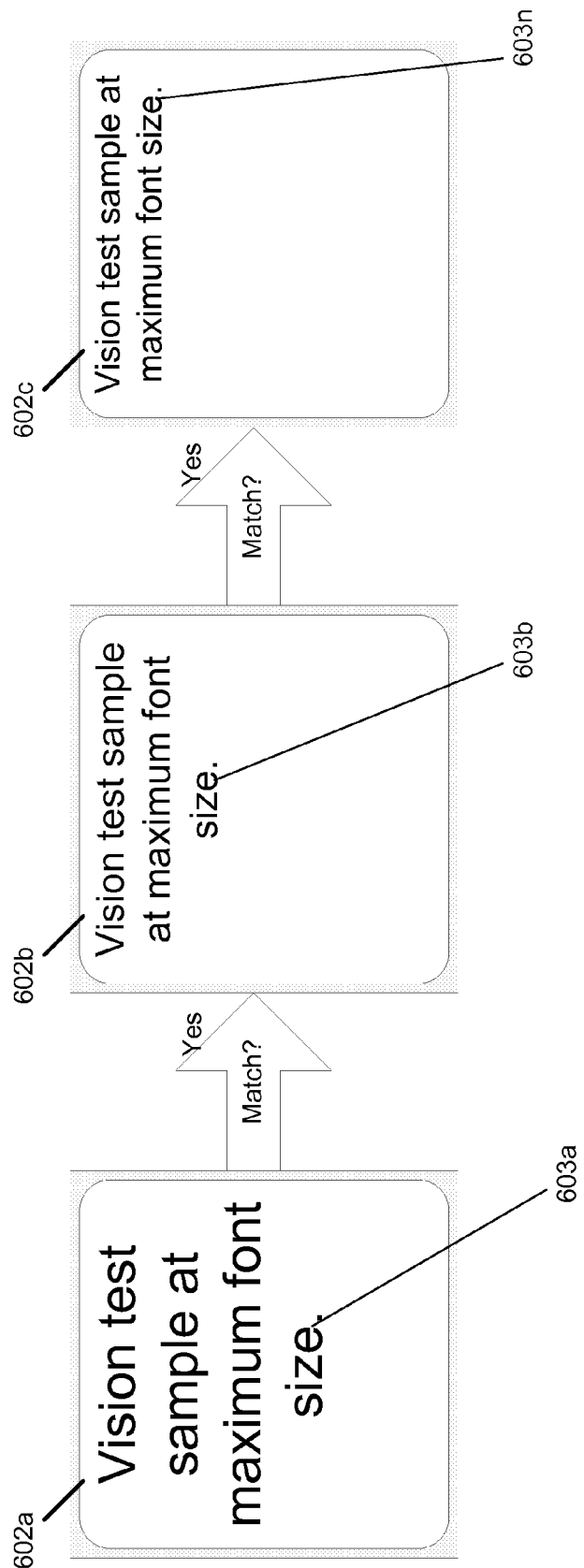
FIG. 6 illustrates an exemplary sequence of vision test character strings, in accordance with one or more embodiments.

Referring now to FIG. 6, there is illustrated an exemplary sequence of vision test character strings, in accordance with one or more embodiments of the present disclosure. As shown, character string 602*a* is displayed at font size 603*a*. As provided above with respect to method 500, after character string 602*a* is displayed at a current font size 603*a* during a vision test, IHS 100 receives a user entry from a user for character string 602*a* and compares the contents of the user entry to the contents of character string 602*a*. In response to IHS 100 determining the content of the user entry by the user for character string 602*a* matches the content of character string 602*a*, font size 603*a* of character string 602*a* is adjusted to a next smallest size and is output as character string 602*b* at font size 603*b*. IHS 100 may then receive a user entry from the user for character string 602*b* and compare the contents of the user entry to the contents of character string 602*b*. In response to IHS 100 determining the content of the user entry by the user for character string 602*b* matches the content of character string 602*b*, font size 603*b* of character string 602*b* is adjusted to a next smallest size and is output as character string 602*c* at font size 603*c*. The process continues in this manner until a smallest font size is reached or until the user entry by the user does not match the current character string.

While character strings 602*a-n* are illustrated as a sentence, a character string may be any arrangement of any combination of letters, numbers, punctuation, and symbols. For example, the character string may be a Snellen eye test chart or one or more sentences. Additionally, each character string displayed may be a unique. For example, each character string may be a different Snellen eye test chart or sentence in order to prevent a user from memorizing a character string. Alternatively, the same character string may be displayed each time the font size is decreased.

Figure 7:
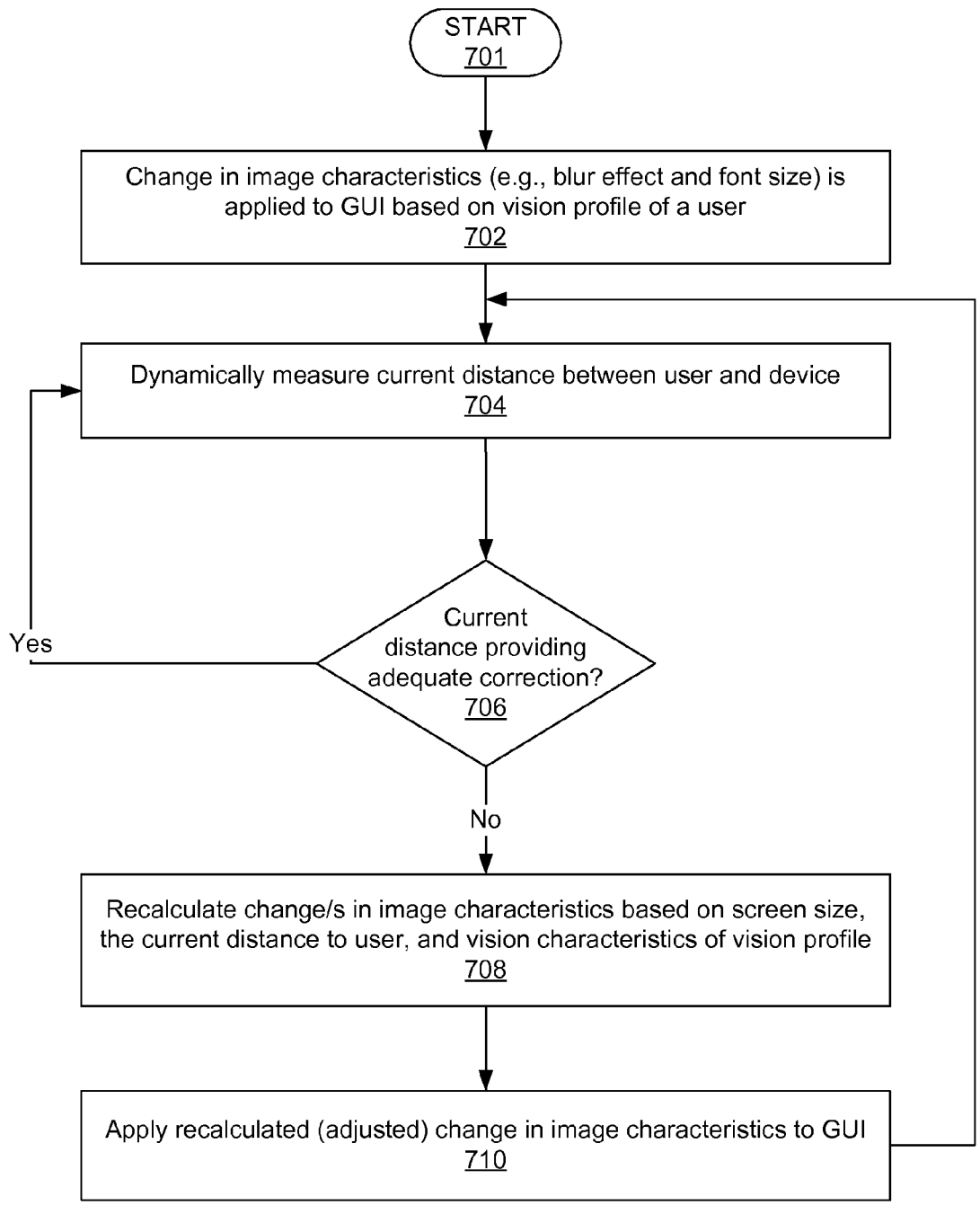
FIG. 7 is a flow chart illustrating a method for recalculating a change in image characteristics of a graphical user interface based on a current distance of a user from an information handling system, in accordance with one or more embodiments.

Referring now to FIG. 7, there is depicted a high-level flow-chart illustrating a method 700 for dynamically recalculating a change in image characteristics of a GUI based on a current distance of a user from an information handling system, in accordance with one or more embodiments of the present disclosure. Method 500 commences at initiator block 701, which proceeds to block 702 where a particular change in image characteristics, such as a blur effect and/or font size, specified within a vision profile that is associated with a user of IHS 100 is applied to the GUI of IHS 100. At block 704 a current distance between the user and IHS 100 is measured. IHS 100 then determines whether current change in image characteristics applied to the GUI are providing adequate correction of undesirable vision characteristics of the user at the current distance between the user and IHS 100 (block 706). In response to determining the current change in image characteristics applied to the GUI are providing adequate correction, the process loops back to block 704.

In response to determining the current change in image characteristics applied to the GUI are not providing adequate correction of the undesirable vision characteristics of the user at the current distance, the change in image characteristics that should be applied to the GUI to best overcome and/or mitigate the undesirable vision characteristics of the user is recalculated based on the contents of the vision profile of the user, the current distance, and the screen size of IHS 100 (block 708). The recalculated change in image characteristics is then applied to the GUI as the adjusted image characteristics (step 710). The process then loops back to block 704. In one embodiment, the font size of the GUI may also be adjusted during the recalculation step, based on the contents of the vision profile of the user, the current distance, and the screen size of IHS 100, in order to best overcome and/or mitigate the undesirable vision characteristics of the user.

In one embodiment the dynamic measurement of the current distance and the determination of whether current change in image characteristics applied to the GUI are adequate are performed at a periodic time interval. In one embodiment the current change in image characteristics applied to the GUI may only be further adjusted based on the current distance when the current distance passes a particular distance threshold from the distance in which the vision test was performed. In another embodiment still, the recalculation may also consider the current display size of IHS 100 versus the display size of the device on which the vision test was performed.

Figure 8:
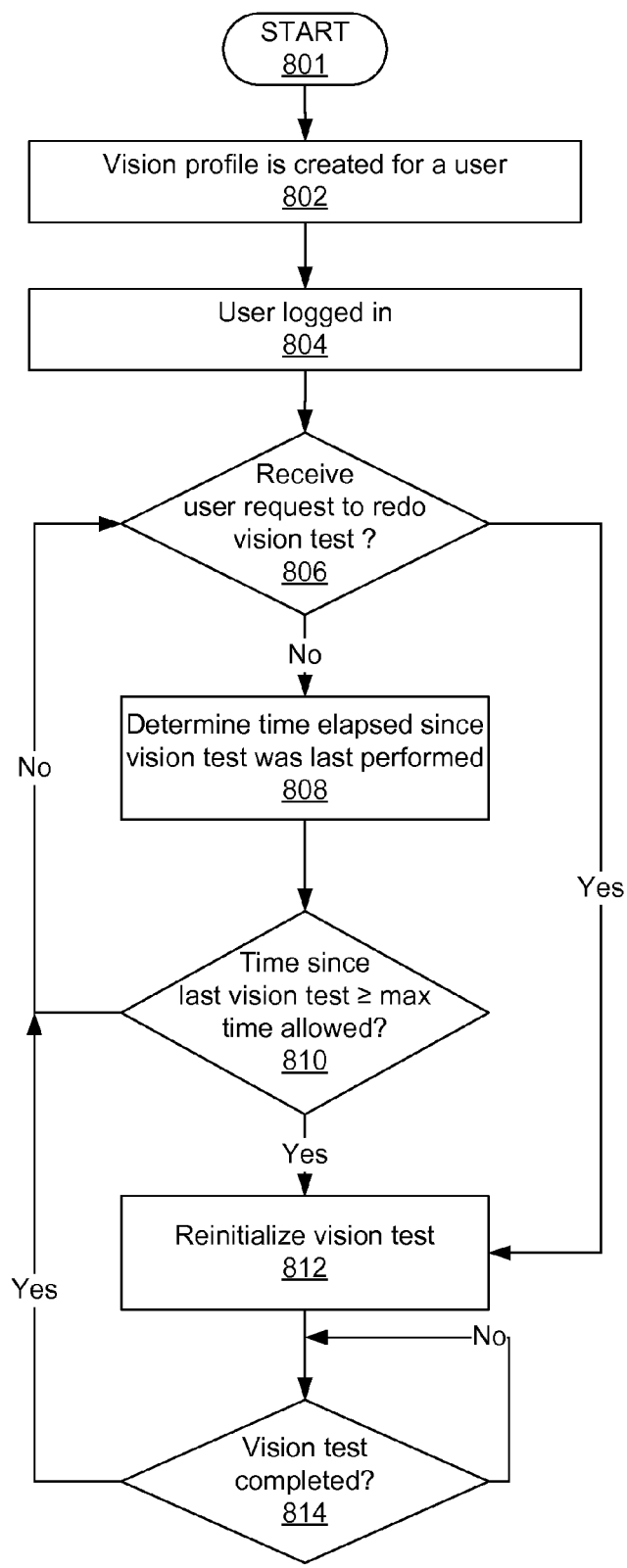
FIG. 8 is a flow chart illustrating a method for reinitializing a vision test on an information handling system, in accordance with one or more embodiments.

Referring now to FIG. 8, there is depicted a high-level flow-chart illustrating a method 800 for reinitializing a vision test on an information handling system, in accordance with one or more embodiments of the present disclosure. Method 800 commences at block 801, which proceeds to block 802 where a vision profile associated with a user profile of a user is created. At block 804 the user profile is logged in to IHS 100. IHS 100 then determines whether a user request to redo a vision test has been received (block 806). In response to a determination that a request to redo a vision test has been received, the vision test is reinitialized (block 812) and the method continues to block 814.

In response to a determination that a request to redo a vision test has not been received, a determination is made if a time since the previous vision test for the user was last performed/completed has reached a maximum time allowed (block 808). In response to determining the time since the previous vision test for the user was last performed/completed has not reached the maximum time allowed, the method loops back to block 806. In response to determining the time since the previous vision test for the user was last performed/completed has reached the maximum time allowed, the method continues to block 812 where the vision test is reinitialized 812. The process then continues to block 814.

At block 814, IHS 100 determines whether the reinitialized vision test has completed. The method does not proceed until the vision test has completed. In response to determining the reinitialized vision test has completed, the method loops back to block 806.

Figure 10:
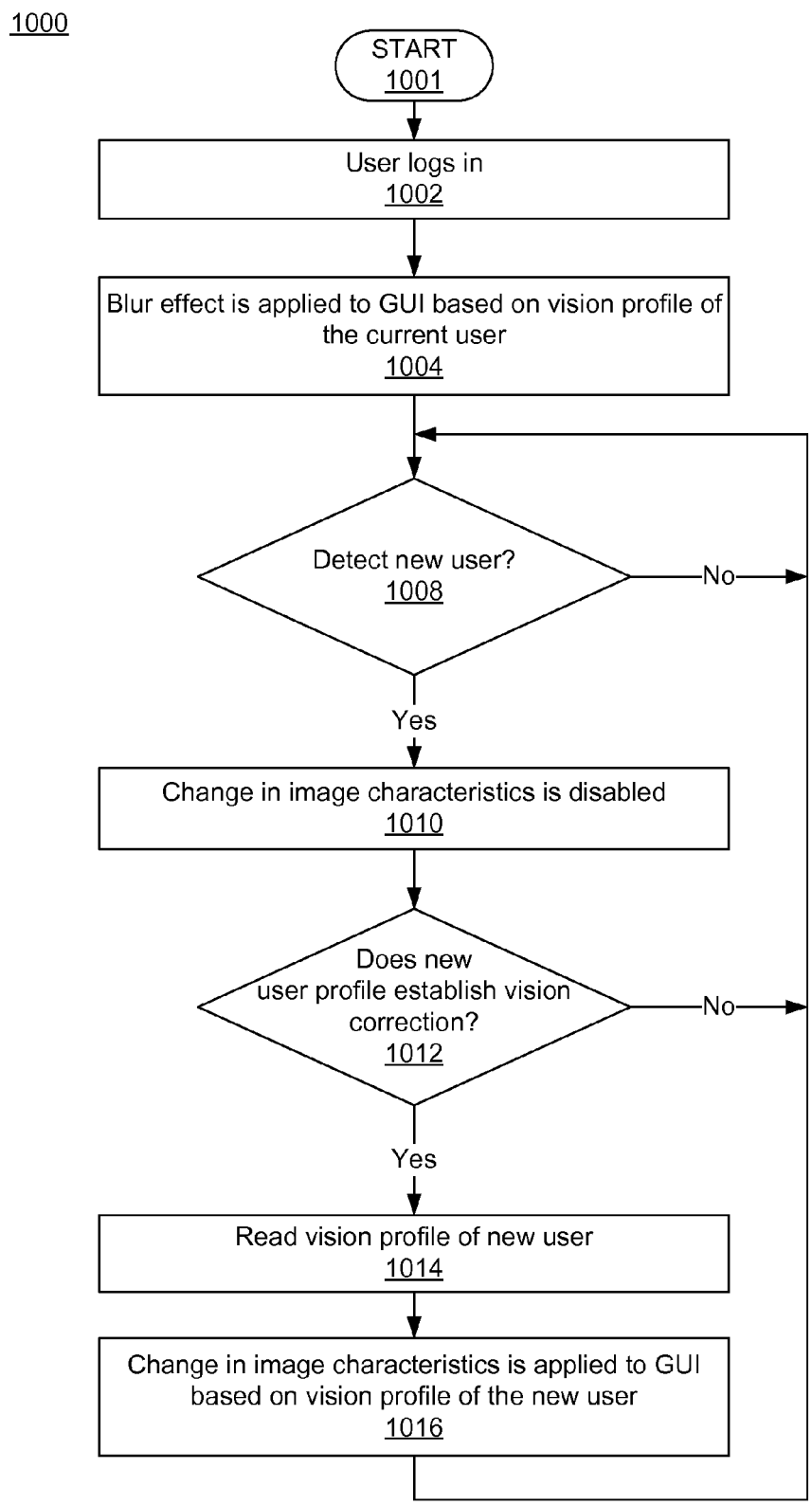
FIG. 10 is a flow chart illustrating a method for detecting a new user of an information handling system, in accordance with one or more embodiments.

Referring now to FIG. 10, there is depicted a high-level flow-chart illustrating a method 1000 for detecting a new user of an information handling system, in accordance with one or more embodiments of the present disclosure. Method 1000 commences at block 1001, and proceeds to block 1002 where a login of a user profile with a vision profile associated with a first user is detected. A change in image characteristics is then applied to the GUI of IHS 100 based on the vision profile of the first user (block 1004). The method then continues to block 1008 where IHS 100 continually scans for a new user. Once a new user has been detected, the change in image characteristics applied to the GUI based on the vision profile of the first user is disabled (block 1010). It is then determined whether a vision profile that includes a vision correction value has been previously established for the new user (block 1012). In response to determining a vision profile that includes a vision correction value for the new user has not been established, the method loops back to block 1008.

In response to determining a vision profile that includes a vision correction value for the new user has been established, the vision profile of the new user is then read (block 1014). A change in image characteristics is then applied to the GUI of IHS 100 based on the vision profile of the new user (block 1016) and the method loops back to block 1008.

In one embodiment the detection of the first user or the new user may be simply identifying that the first user or new user is present (e.g., facial recognition by a camera of IHS 100). In another embodiment, detecting a user requires the user login to IHS 100. In the embodiment in which the same user has a baseline profile (e.g., with contact lenses) and a corrective profile (e.g., without contact lenses), the detection of a new user may be a detection that the first user has removed his/her contacts. The corrective profile is then loaded in place of the baseline profile. It is appreciated that the baseline profile introduced within the description of the embodiments may in fact be the normal display of the screen (i.e., no actual changes to the display characteristics) and not an actual separately stored profile, as no correction is required, in certain instances, when the user is wearing his/her contact lenses.

Figure 11:
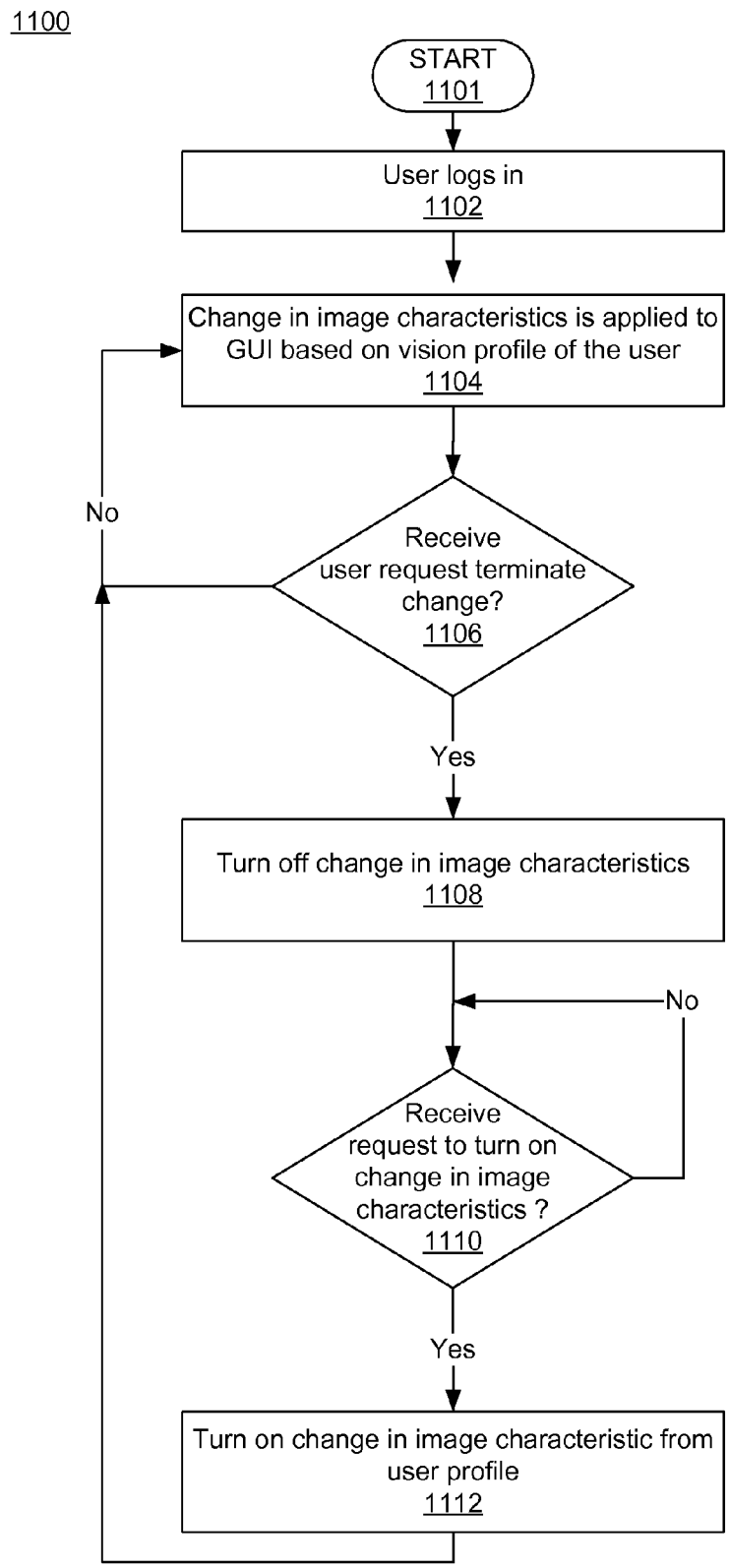
FIG. 11 is a flow chart illustrating a method for terminating a change in image characteristics of a graphical user interface responsive to receiving a user request, in accordance with one or more embodiments.

Referring now to FIG. 11, there is depicted a high-level flow-chart illustrating a method 1100 for terminating a change in image characteristics of a graphical user interface responsive to receiving a user request, in accordance with one or more embodiments of the present disclosure. After initiator block 1101 a user logs in to IHS 100 (block 1102). A change in image characteristics is then applied to the GUI of IHS 100 based on the vision profile of that user (block 1104). At block 1106 IHS 100 determines whether a request to terminate the applied change in image characteristics has been received. Once a request to terminate the applied change in image characteristics has been received, the method continues to block 1108 where the applied change in image characteristics is turned off or disabled. At block 1110 IHS 100 determines whether a request to reapply the change in image characteristics has been received. Once a request to reapply the change in image characteristics has been received, the method continues to block 1112 where the change in image characteristics is turned on or re-enabled. The method then loops back to block 1104.

Figure 12:
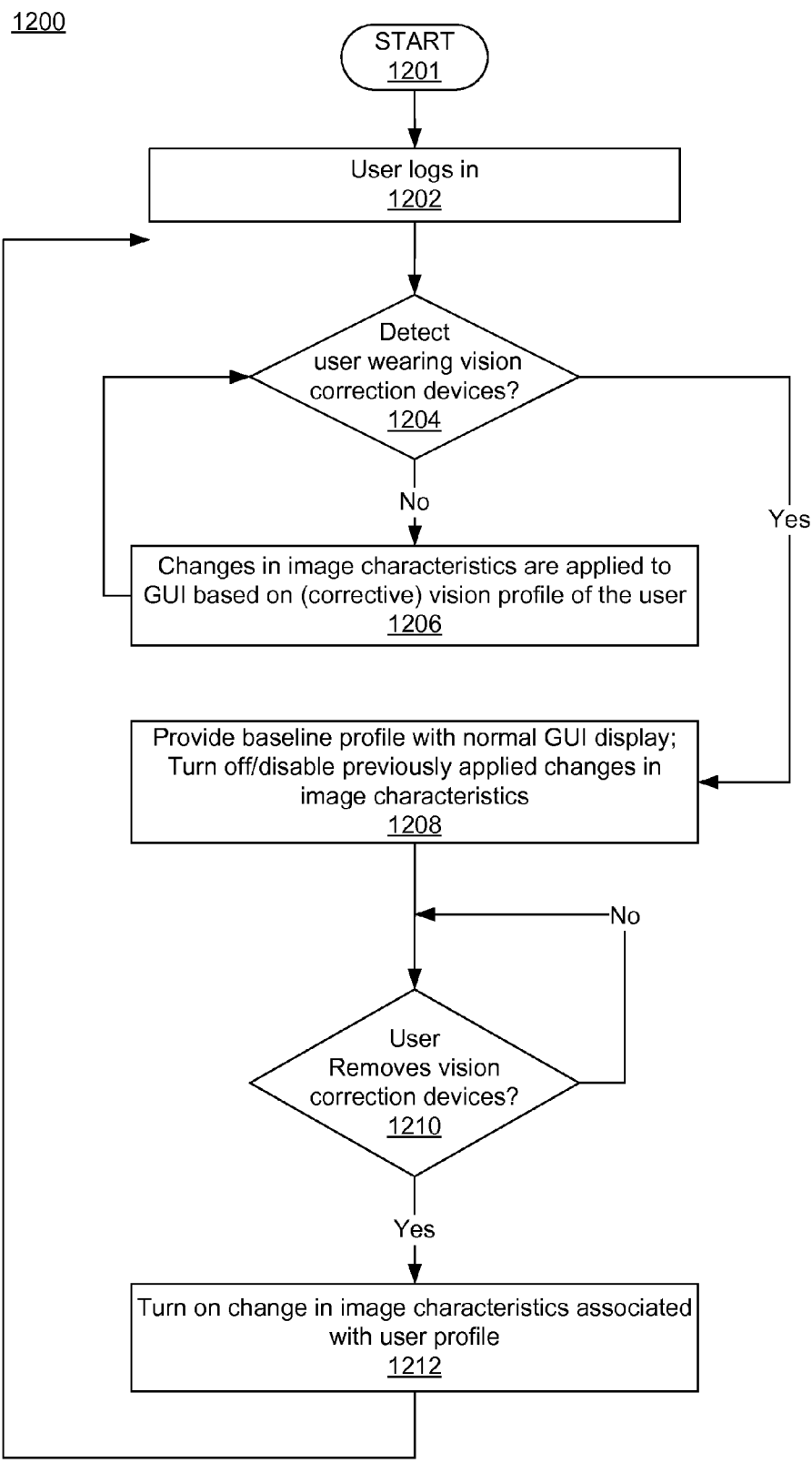
FIG. 12 is a flow chart illustrating a method for terminating a change in image characteristics of a graphical user interface responsive to detecting a user wearing a vision correction device, in accordance with one or more embodiments.

Referring now to FIG. 12, there is depicted a high-level flow-chart illustrating a method 1200 for terminating a change in image characteristics of a graphical user interface responsive to detecting a user wearing a vision correction device, in accordance with one or more embodiments of the present disclosure. After initiator block 1201 a user logs in to IHS 100 (block 1202). At block 1204 IHS 100 determines whether the user is wearing any vision correction devices. In response to determining that the user is not wearing vision correction devices, changes in image characteristics are applied to the GUI of IHS 100 based on the vision profile of that user (block 1206). HIS 100 continues to monitor the user for use of the vision correction devices. In response to determining the user is wearing vision correction devices, the method continues to block 1208 where the IHS 100 provides a baseline profile with normal GUI display and/or any previously applied change in image characteristics is automatically turned off or disabled. At block 1210 IHS 100 determines whether the user has removed all worn vision correction devices. In response to determining the user has removed all worn vision correction devices, the method continues to block 1212 where the change in image characteristics from the user's profile is turned on/re-enabled. The method then loops back to block 1206.

In another embodiment, in response to determining the user is wearing vision correction devices, IHS 100 further issues a prompt to the user, using one or more of audio, visual, and/or vibration feedback, that identifies to the user that vision correction devices have been detected and provides selection options to enable the user to turn off/disable the change in image characteristics or leave the change in image characteristics turned on/enabled.

In the above described flow charts, one or more of the method processes may be embodied in a computer readable device containing computer readable code such that a series of steps are performed when the computer readable code is executed on a computing device. In some implementations, certain steps of the methods are combined, performed simultaneously or in a different order, or perhaps omitted, without deviating from the scope of the disclosure. Thus, while the method steps are described and illustrated in a particular sequence, use of a specific sequence of steps is not meant to imply any limitations on the disclosure. Changes may be made with regards to the sequence of steps without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, such as a GPU, or other programmable data processing apparatus to produce a machine, such that the instructions, which execute via the processor of the computer or other programmable data processing apparatus, performs the method for implementing the functions/acts specified in the flowchart and/or block diagram block or blocks.

As will be further appreciated, the processes in embodiments of the present disclosure may be implemented using any combination of software, firmware or hardware. Accordingly, aspects of the present disclosure may take the form of an entirely hardware embodiment or an embodiment combining software (including firmware, resident software, microcode, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method comprising:
   detecting, at an information handling system, a login of a first user profile of one or more user profiles, wherein the first user profile is associated with a first user;
   in response to detecting the login of the first user profile, determining whether the first user profile has an associated first vision profile; and
   in response to the first user profile having an associated first vision profile:
      identifying, from the first vision profile, a vision correction value associated with the first user;
      calculating a first change in image characteristics that may be applied to a graphical user interface (GUI) in order to achieve the vision correction value;
      detecting a size of the display of the information handling system;
      adjusting the first change in image characteristics based on the size of the display to generated adjusted image characteristics; and
      applying one of the first change in image characteristics and the adjusted image characteristics to the GUI, wherein the GUI is displayed on a display of the information handling system with at least the first change in image characteristics applied to one or more content of the GUI.

2. The method of claim 1, wherein the information handling system has a user-facing camera, and wherein detecting the login by the first user profile further comprises:
   dynamically detecting a presence of a current user of the information handling system;
   performing, with the user-facing camera, a facial recognition of the current user of the information handling system;
   comparing identifying characteristics from the facial recognition of the current user with facial recognition profiles known to the information handling system to determine whether any of the facial recognition profiles includes identifying characteristics that match characteristics from the facial recognition of the current user; and
   in response to finding a match of identifying characteristics from a facial recognition profile of the first user from among the facial recognition profiles:
      identifying the current user as the first user; and
      logging the first user profile in to at least one software running on the information handling system that generates the GUI.

3. The method of claim 2, further comprising:
   dynamically measuring, via the user-facing camera, a distance between the first user and the information handling system; and
   dynamically adjusting the first change in image characteristics to the GUI based on the distance between the first user and the information handling system.

4. The method of claim 1, further comprising:
   in response to determining the first user profile does not have an associated vision profile, establishing the associated vision profile for the first user profile, wherein establishing the associated vision profile further comprises:
      setting a font size of the GUI to a largest size;
      performing a vision test comprising:
         displaying a character string on the display, wherein the character string comprises one or more alphanumeric values and symbols from among letters, numbers, and punctuation;
         requesting the first user reenter the displayed character string;
         receiving a user entry in response to the request;
         in response to receiving the user entry, determining whether the user entry is a match to the displayed character string;
         in response to determining the user entry is a match to the displayed character string: adjusting the font size of the GUI to a next smaller size and reinitializing the vision test; and
         in response to determining the user entry of the character string is not a match to the displayed character string: creating the associated vision profile of the first user profile and recording, within the associated vision profile for the first user profile, a plurality of vision characteristics based on the vision test and a smallest size of the font size that was correctly identified by the first user.

5. The method of claim 4, further comprising:
   detecting whether the first user is wearing at least one of corrective contact lenses and corrective lenses;
   in response to detecting that the first user is wearing corrective lenses:
      requesting the first user remove the corrective lenses before initializing the vision test; and
      preventing initialization of the vision test until it has been detected that the first user is not wearing corrective lenses; and
   in response to detecting that the first user is wearing corrective contact lenses, postponing the vision test unless the user requests the vision test and removes the corrective contact lenses.

6. The method of claim 4, wherein the information handling system includes a microphone and the vision test supports a verbal recitation of the character string, the method further comprising:
   recording the verbal recitation of the user entry of the character string via the microphone; and
   performing an audio analysis of the recorded verbal recitation to determine a spoken content of the recorded verbal recitation, wherein the spoken content is the user entry of the character string.

7. The method of claim 1, further comprising:
   detecting whether the first user is wearing at least one of corrective contact lenses and corrective lenses; and
   in response to detecting that the first user is wearing at least one of corrective contact lenses and corrective lenses:
      removing the application of the first change in image characteristics from the GUI;
      periodically monitoring for removal by the user of the at least one of corrective contact lenses and corrective lenses; and
      in response to detecting that the first user is no longer wearing the at least one of the corrective contact lenses and the corrective lenses, re-applying the first change in image characteristics to the GUI.

8. An information handling system comprising:
   a least one processing device;
   a memory;
   a digital display correction utility that when executed by the at least one processing device, enables the information handling system:
   detect, at an information handling system, a login of a first user profile of one or more user profiles, wherein the first user profile is associated with a first user;
   in response to detecting the login of the first user profile, determine whether the first user profile has an associated first vision profile; and
   in response to the first user profile having an associated first vision profile:
   identify, from the first vision profile, a vision correction value associated with the first user;
   calculate a first change in image characteristics that may be applied to a graphical user interface (GUI) in order to achieve the vision correction value;
   detect a size of the display of the information handling system;
   adjust the first change in image characteristics based on the size of the display to generate adjusted image characteristics; and
   apply the first change in image characteristics to the GUI, wherein the GUI is displayed on a display of the information handling system with the first change in image characteristics applied to one or more content of the GUI.

9. The information handling system of claim 8, further comprising a user-facing camera, wherein detecting the login by the first user profile further comprises:
   dynamically detect a presence of a current user of the information handling system;
   perform, with the user-facing camera, a facial recognition of the current user of the information handling system;
   compare identifying characteristics from the facial recognition of the current user with facial recognition profiles known to the information handling system to determine whether any of the facial recognition profiles includes identifying characteristics that match characteristics from the facial recognition of the current user; and
   in response to finding a match of identifying characteristics from a facial recognition profile of the first user from among the facial recognition profiles:
   identify the current user as the first user; and
   log the first user profile in to at least one software running on the information handling system that generates the GUI.

10. The information handling system of claim 9, the digital display correction utility further comprising instructions that enable the information handling system to:
    dynamically measure, via the user-facing camera, a distance between the first user and the information handling system; and
    dynamically adjust the first change in image characteristics to the GUI based on the distance between the first user and the information handling system.

11. The information handling system of claim 8, further comprising:
    in response to determining the first user profile does not have an associated vision profile, establish the associated vision profile for the first user profile, wherein establishing the associated vision profile further comprises:
    set a font size of the GUI to a largest size; and
    perform a vision test comprising:
    display a character string on the display, wherein the character string comprises one or more alphanumeric values and symbols from among letters, numbers, and punctuation;
    request the first user reenter the displayed character string;
    receive a user entry in response to the request;
    in response to receiving the user entry, determine whether the user entry is a match to the displayed character string;
    in response to determining the user entry is a match to the displayed character string: adjust the font size of the GUI to a next smaller size and reinitializing the vision test; and
    in response to determining the user entry of the character string is not a match to the displayed character string: create the associated vision profile of the first user profile and record, within the associated vision profile for the first user profile, a plurality of vision characteristics based on the vision test and a smallest size of the font size that was correctly identified by the first user.

12. The information handling system of claim 11, the digital display correction utility further comprising instructions that enable the information handling system to:
    detect whether the first user is wearing at least one of corrective contact lenses and corrective lenses;
    in response to detecting that the first user is wearing corrective lenses:
    request the first user remove the corrective lenses before initializing the vision test; and prevent initialization of the vision test until it has been detected that the first user is not wearing the at least one of corrective contact lenses and corrective lenses;
    in response to detecting that the first user is wearing corrective contact lenses, postpone the vision test unless the user requests the vision test and removes the corrective contact lenses; and
    in response to detecting that the first user is wearing at least one of corrective contact lenses and corrective lenses:
    remove the application of the first change in image characteristics from the GUI;
    periodically monitor for removal by the user of the at least one of corrective contact lenses and corrective lenses; and
    in response to detecting that the first user is no longer wearing the at least one of the corrective contact lenses and the corrective lenses, re-apply the first change in image characteristics to the GUI.

13. The information handling system of claim 11, wherein the user entry of the character string is a verbal recitation of the character string, the digital display correction utility further comprising instructions that enable the information handling system to:
    record the verbal recitation of the user entry of the character string via the microphone; and
    perform an audio analysis of the recorded verbal recitation to determine a spoken content of the recorded verbal recitation, wherein the spoken content is the user entry of the character string.

14. A computer program product comprising:
    a computer readable storage device; and
    program code embedded on the computer readable storage device that when executed by a processor of an information handling system performs the following functions:
    detecting, at an information handling system, a login of a first user profile of one or more user profiles, wherein the first user profile is associated with a first user;
    in response to detecting the login of the first user profile, determining whether the first user profile has an associated first vision profile; and in response to the first user profile having an associated first vision profile:
  identifying, from the first vision profile, a vision correction value associated with the first user;
  calculating a first change in image characteristics that may be applied to a graphical user interface (GUI) in order to achieve the vision correction value;
  detecting a size of the display of the information handling system;
  adjusting the first change in image characteristics based on the size of the display to generate adjusted image characteristics; and
  applying the adjusted image characteristics to the GUI, wherein the GUI is displayed on a display of the information handling system with the adjusted image characteristics applied to one or more content of the GUI.

15. The computer program product of claim 14, wherein the information handling system further comprises a user-facing camera, and wherein the program code for detecting the login by the first user profile further comprises program code that provides the following functions:
  dynamically detecting a presence of a current user of the information handling system;
  performing, with the user-facing camera, a facial recognition of the current user of the information handling system;
  comparing identifying characteristics from the facial recognition of the current user with facial recognition profiles known to the information handling system to determine whether any of the facial recognition profiles includes identifying characteristics that match characteristics from the facial recognition of the current user; and
  in response to finding a match of identifying characteristics from a facial recognition profile of the first user from among the facial recognition profiles:
    identifying the current user as the first user; and
    logging the first user profile in to at least one software running on the information handling system that generates the GUI.

16. The computer program product of claim 15, the program code further providing the following functions:
  dynamically measuring, via the user-facing camera, a distance between the first user and the information handling system; and
  dynamically adjusting the first change in image characteristics to the GUI based on the distance between the first user and the information handling system.

17. The computer program product of claim 14, wherein the program code further provides the following functions:
  in response to determining the first user profile does not have an associated vision profile, establishing the associated vision profile for the first user profile, wherein establishing the associated vision profile further comprises:
    setting a font size of the GUI to a largest size;
    performing a vision test comprising:
      displaying a character string on the display, wherein the character string comprises one or more alphanumeric values and symbols from among letters, numbers, and punctuation;
      requesting the first user reenter the displayed character string;
      receiving a user entry in response to the request;
      in response to receiving the user entry, determining whether the user entry is a match to the displayed character string;
      in response to determining the user entry is a match to the displayed character string: adjusting the font size of the GUI to a next smaller size and reinitializing the vision test; and
      in response to determining the user entry of the character string is not a match to the displayed character string: creating the associated vision profile of the first user profile and recording, within the associated vision profile for the first user profile, a plurality of vision characteristics based on the vision test and a smallest size of the font size that was correctly identified by the first user.

18. The computer program product of claim 17, the program code further providing the following functions:
  detecting whether the first user is wearing at least one of corrective contact lenses and corrective lenses;
  in response to detecting that the first user is wearing corrective lenses:
    requesting the first user remove the corrective lenses before initializing the vision test; and
    preventing initialization of the vision test until it has been detected that the first user is not wearing the at least one of corrective contact lenses and corrective lenses; and
  in response to detecting that the first user is wearing corrective contact lenses, postponing the vision test unless the user requests the vision test and removes the corrective contact lenses.

19. The computer program product of claim 17, wherein the information handling system includes a microphone and the vision test supports a verbal recitation of the character string, the program code further providing the following functions:
  recording the verbal recitation of the user entry of the character string via the microphone; and
  performing an audio analysis of the recorded verbal recitation to determine a spoken content of the recorded verbal recitation, wherein the spoken content is the user entry of the character string.

20. The computer program product of claim 14, the program code further providing the following functions:
  detecting whether the first user is wearing at least one of corrective contact lenses and corrective lenses; and
  in response to detecting that the first user is wearing at least one of corrective contact lenses and corrective lenses:
    removing the application of the first change in image characteristics to the GUI;
    periodically monitoring for removal by the user of the at least one of corrective contact lenses and corrective lenses; and
    in response to detecting that the first user is no longer wearing the at least one of the corrective contact lenses and the corrective lenses, re-applying the first change in image characteristics to the GUI.

* * * * *